United States Patent
Labyed et al.

(10) Patent No.: US 11,129,598 B2
(45) Date of Patent: Sep. 28, 2021

(54) CALIBRATION FOR ARFI IMAGING

(71) Applicant: Siemens Medical Solutions USA, Inc., Malvern, PA (US)

(72) Inventors: Yassin Labyed, Maple Valley, WA (US); John Benson, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 237 days.

(21) Appl. No.: 15/841,177

(22) Filed: Dec. 13, 2017

(65) Prior Publication Data

US 2019/0175150 A1 Jun. 13, 2019

(51) Int. Cl.
*A61B 8/14* (2006.01)
*A61B 8/00* (2006.01)
(Continued)

(52) U.S. Cl.
CPC .................. *A61B 8/58* (2013.01); *A61B 8/14* (2013.01); *A61B 8/4416* (2013.01); *A61B 8/463* (2013.01);
(Continued)

(58) Field of Classification Search
None
See application file for complete search history.

(56) References Cited

U.S. PATENT DOCUMENTS 9,332,962 B2 5/2016 Kim et al.
9,332,963 B2 5/2016 Ivancevich et al.
(Continued)

FOREIGN PATENT DOCUMENTS

| CN | 103800038 | 5/2014 |
|---|---|---|
| JP | 2010046484 | 3/2010 |
| KR | 20170115964 | 10/2017 |

OTHER PUBLICATIONS

Nightingale, Kathryn et al., "Analysis of Contrast in Images Generated With Transient Acoustic Radiation Force", Ultrasound in Medicine & Biology, vol. 32, No. 1, 2006, 12 pp.
(Continued)

*Primary Examiner* — Christopher Koharski
*Assistant Examiner* — Jillian K. McGough

(57) ABSTRACT

A system and method includes transmission of an ultrasound push pulse toward material along a first axis, the ultrasound push pulse associated with a first frequency, a first F number, and a first focal depth, determination of displacement of the material along the axis in response to the push pulse, transmission of a second ultrasound pulse toward the material along the first axis, the second ultrasound pulse associated with a second frequency, a second F number, and a second focal depth substantially similar to the first frequency, the first F number, and the first focal depth, respectively, reception of echo signals from the material in response to the second ultrasound pulse, beamforming of the echo signals based on the first F number and a fixed focus at the first focal depth, determination of a magnitude of the beamformed echo signals along the axis, determination of relative elasticity of the material along the axis based on the determined displacement of the material along the axis and the magnitude of the beamformed echo signals along the axis, and generation of an image based on the determined relative elasticity of the material along the axis.

14 Claims, 8 Drawing Sheets

(51) Int. Cl.
   *G01S 7/52* (2006.01)
   *G01S 15/89* (2006.01)
   *A61B 8/08* (2006.01)

(52) U.S. Cl.
   CPC ............ *A61B 8/485* (2013.01); *A61B 8/5207* (2013.01); *A61B 8/5223* (2013.01); *A61B 8/5246* (2013.01); *A61B 8/54* (2013.01); *G01S 7/52022* (2013.01); *G01S 7/52042* (2013.01); *G01S 7/52046* (2013.01); *G01S 7/52063* (2013.01); *G01S 15/8952* (2013.01)

(56) References Cited

U.S. PATENT DOCUMENTS

| | | | |
|---|---|---|---|
| 10,376,233 | B2 | 8/2019 | Fan et al. |
| 2005/0215899 | A1 | 9/2005 | Fahey et al. |
| 2011/0184287 | A1* | 7/2011 | McAleavey ......... A61B 8/4483 600/438 |
| 2012/0134233 | A1* | 5/2012 | Lin .................... G01S 7/52022 367/7 |
| 2013/0218011 | A1* | 8/2013 | Benson ................ A61B 8/485 600/438 |
| 2015/0141822 | A1* | 5/2015 | Miyauchi .............. G06T 7/0012 600/438 |
| 2015/0223778 | A1* | 8/2015 | Honjo ..................... A61B 8/54 600/447 |
| 2016/0228090 | A1* | 8/2016 | Boctor ................ A61B 8/4416 |
| 2017/0156705 | A1* | 6/2017 | Galluzzo ............... A61B 90/37 |
| 2017/0347990 | A1* | 12/2017 | Watanabe .............. A61B 8/461 |

OTHER PUBLICATIONS

Zhai, Liang et al., "Acoustic Radiation Force Impulse Imaging of Human Prostates", NIH Public Access, Author Manuscript, Ultrasound Med Biol, Apr. 2010, 23 pp.

Nightingale, Kathy, "Acoustic Radiation Force Impulse (ARFI) Imaging: a Review", NIH Public Access, Author Manuscript, Curr Med Imaging Rev., Nov. 1, 2011, 24 pp.

Benson, John "Tissue Strain Analytics. A Complete Ultrasound Solution for Elastography", Siemens, www.siemens.com/healthcare, copyright Dec. 2012, 20 pp.

* cited by examiner

CALIBRATION FOR ARFI IMAGING

BACKGROUND

A conventional ultrasound imaging system creates an internal image of a volume by detecting acoustic impedance discontinuities within the volume. More specifically, conventional ultrasound imaging involves transmitting ultrasound beams into a volume and detecting signals which reflect from acoustic impedance discontinuities within the volume. Since different materials typically exhibit different acoustic impedances, the detected acoustic impedance discontinuities represent the locations of different materials within the volume.

Stiff tissue and soft tissue (e.g., within a liver) may exhibit similar acoustic impedances. Since only a small acoustic impedance discontinuity may exist between such stiff and soft tissues, ultrasound beams would not reflect significantly at the boundary between the tissues. Accordingly, a conventional ultrasound image would fail to adequately distinguish between the soft tissue and the stiff tissue.

Soft and stiff tissues with similar acoustic impedances may behave differently when subjected to stress. For a given impulsive force, softer tissues move farther, take longer to reach a peak displacement, and recover more slowly than stiffer tissues. Acoustic radiation force impulse (ARFI) imaging exploits these different behaviors to generate images which distinguish tissues based on their relative stiffness. ARFI imaging involves mechanically compressing tissue using an ultrasound "push" pulse and tracking the resulting on-axis tissue displacement. Relative differences in displacement are determined and displayed using grayscale or color coding, thereby depicting the relative stiffness of regions within the tissue.

The intensity of the push pulse within the tissue is depth-dependent and influenced by diffraction and attenuation along the path to the focal region of the push pulse, the focal gain, and absorption properties of the tissue. Since tissue displacement is proportional to intensity gradients within the tissue, an ARFI-generated displacement profile of homogeneous tissue will misleadingly depict greater displacement (i.e., stiffer tissue) at the focus and at shallow depths.

Conventional ARFI systems attempt to normalize the displacement profile of a region of interest (i.e., an ARFI image) based on intensity gradients within the region. For example, a displacement profile of a homogeneous phantom is generated using a push pulse having the same focus as the displacement profile of the region of interest. The displacement profile of the region of interest is then normalized by dividing out the displacement profile of the homogeneous phantom. This approach fails to account for the intensity gradients within the specific tissue of the region of interest. Systems are desired to calibrate an ARFI image based on actual intensity gradients within the imaged tissue.

BRIEF DESCRIPTION OF THE DRAWINGS

The construction and usage of embodiments will become apparent from consideration of the following specification as illustrated in the accompanying drawings, in which like reference numerals designate like parts, and wherein.

DETAILED DESCRIPTION

The following description is provided to enable any person in the art to make and use the described embodiments and sets forth the best mode contemplated for carrying out the described embodiments. Various modifications, however, will remain apparent to those in the art.

Some embodiments provide efficient and accurate generation of an ARFI image. More specifically, some embodiments provide an inventive system to calibrate an ARFI image based on the actual depth-dependent force applied to the tissue being imaged. Such an image may depict the relative stiffness of imaged tissues more accurately than conventional systems.

A technical problem addressed by some embodiments is the inability of prior ARFI systems to account for the attenuation and diffraction patterns of tissue being imaged. Some embodiments provide a technical solution via specific control of parameters used to acquire a B-mode image and use of the B-mode image to normalize an ARFI image based on the attenuation and diffraction patterns of the imaged tissue.

Figure 1:
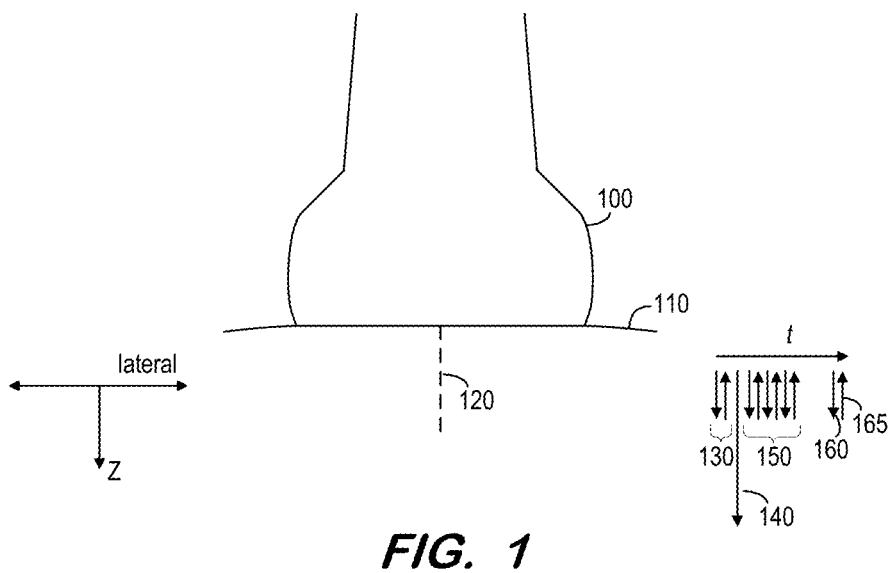
FIG. 1 illustrates a process to generate a calibrated ARFI image according to some embodiments.

FIG. 1 illustrates an implementation according to some embodiments. Generally, ultrasound transducer 100 transmits ultrasound beams into volume 110 and receives ultrasound signals therefrom. Volume 110 may comprise a human body but embodiments are not limited thereto. Ultrasound transducer 100 may comprise any suitable ultrasound transducer, such as but not limited to a phased-array, linear or convex ultrasound transducer.

FIG. 1 depicts acquisition of one line of an ARFI image according to some embodiments. The line extends along axis 120 in the Z-direction from a point on the lateral axis. Each of below-described ultrasound beams 130 through 160 is centered around axis 120, although at different times.

Ultrasound beams 130 through 150 are used to acquire an ARFI image as is known in the art. In particular, transmit/receive beams 130 depict the transmission of a B-mode ultrasound tracking pulse and reception of a corresponding baseline tracking echo signal as is known in the art. The baseline tracking echo signal is intended to measure tissue displacements due to physiological motion along axis 120 prior to an ARFI push pulse. One or more sets of baseline tracking echo signals may be acquired and used (e.g., averaged) to obtain the initial positions. Ultrasound transducer 100 then transmits beam 140 along axis 120. Beam 140 comprises a push pulse intended to displace the tissue along axis 120 and in the direction of axis 120. Transmission of a push pulse is known in the art, and typically consists of many more cycles than a transmit pulse used to generate B-mode data.

Next, ultrasound signals 150 are used to monitor the resulting displacement of the tissue over time. Each received signal or signals 150 is a displacement tracking echo signal which represents a frame of data indicating positions of the tissues at a given point in time. As is known in the art, the displacement tracking echo signals may be cross-correlated to determine a displacement magnitude over time for each point z along axis 120. A motion filter is applied to the temporal displacement profiles to filter out displacements caused by physiological motion. This data is then used to determine a maximum displacement profile which indicates the maximum displacement experienced at each point z.

The displacements tracked by the displacement tracking echo signals are caused by both the ultrasound push pulse and underlying physiological motion. The above-mentioned baseline tracking echo signal may be used to model the underlying physiological motion, which is subtracted from the maximum displacement profile to obtain the maximum displacements caused by the push pulse only. Some embodiments employ 10-20 baseline tracking pulse/echo signal pairs prior to the push pulse in order to obtain a suitable polynomial model of the baseline data.

The physiological motion may also be modeled using, in addition to the baseline tracking described above, tracking signals obtained after the tissue returns to its original state. Fitting a polynomial to the displacement values determined from these tracking signals may provide a better estimate of underlying physiological motion to be filtered out as described above.

Beam 160 and signal 165 are used to acquire additional B-mode data. According to some embodiments, the parameters of transmit beam 160 are substantially similar to those of push pulse 140. For example, transmit beam 160 may be generated using frequency, F-number/aperture size, focus and apodization function parameters which are similar to those of push pulse 140. The number of cycles of transmit beam 160 is suitable to exhibit a narrow frequency band (e.g., 2-8 cycles). In contrast, push pulse 140 may consist of hundreds of cycles.

Receive signal 165 is a backscatter signal and is received using a fixed focus, as opposed to conventional dynamic receive beamforming. The fixed focus location is substantially similar to the focus of push pulse 140 and transmit beam 160. The amplitude of receive signal 165 is then determined as a function of Z.

The maximum displacement profile is normalized by the amplitude of receive signal 165 as a function of Z. According to some embodiments, normalization consists of dividing the maximum displacement profile by the amplitude of receive signal 165. As will be described in detail below, the resulting function represents the relative stiffness of tissues along axis 120, while reducing artifacts in the maximum displacement profile caused by attenuation and diffraction effects within the imaged tissue.

Figure 2:
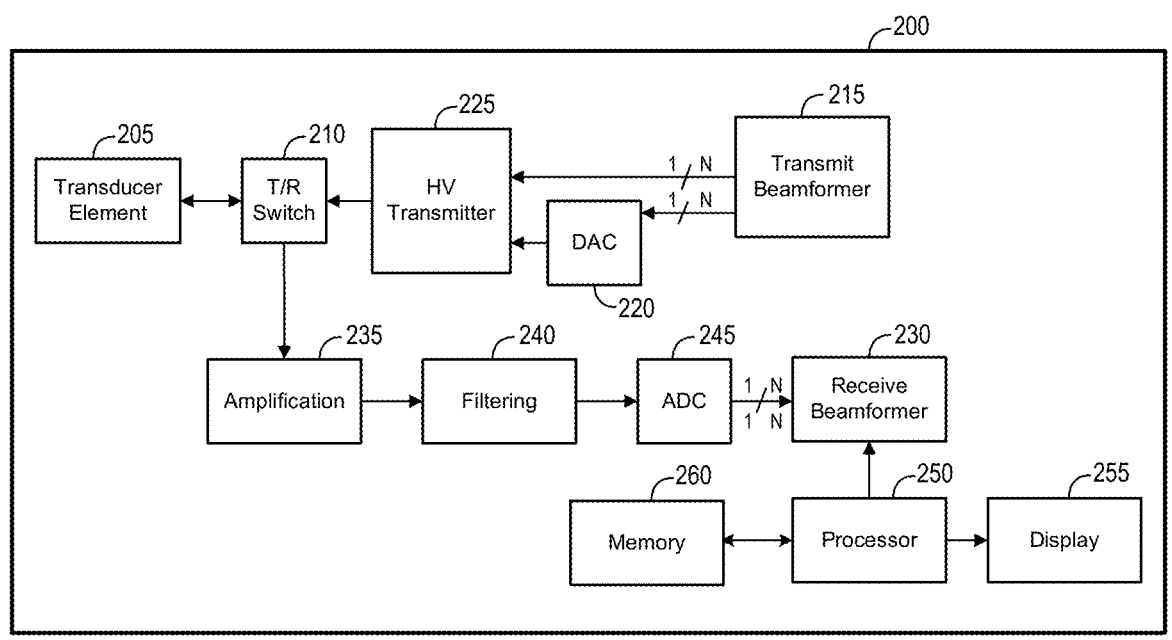
FIG. 2 is a block diagram of an ultrasound imaging apparatus according to some embodiments.

FIG. 2 is a block diagram of ultrasound imaging system 200 according to some embodiments. System 200 may implement one or more of the processes described herein. System 200 is a phased-array ultrasound imaging system, but embodiments are not limited thereto. Typical phased array systems utilize 64 to 256 receive channels and a comparable number of transmit channels. For clarity, FIG. 2 illustrates a single transmit-and-receive channel.

System 200 comprises transducer element 205 and transmit/receive switch 210. Transducer element 205 may comprise an element of a 1-, 1.25-, 1.5-, 1.75- or 2-dimensional array of piezoelectric or capacitive membrane elements. Transmit/receive switch 210 is operated to either allow transmission of ultrasonic energy via element 205 (e.g., in response to application of a voltage across element 205), or to allow reception of a voltage generated by element 205 in response to received ultrasonic energy (i.e., echoes).

Transmit beamformer 215 is operable, in conjunction with digital-to-analog converter 220 and high-voltage transmitter 225, to generate waveforms for a plurality of channels, where each waveform may exhibit a different amplitude, delay, and/or phase. Receive beamformer 230 receives signals from a plurality of channels, each of which may be subjected to amplification 235, filtering 240, analog-to-digital conversion 245, delays and/or phase rotators, and one or more summers. Receive beamformer 230 may be configured by hardware or software to apply relative delays, phases, and/or apodization to form one or more receive beams in response to each transmit beam. Receive beamformer 230 may provide dynamic receive focusing as is known in the art, as well as fixed focus reception.

The receive beams formed by receive beamformer 230 represent the material through which the transmit beams and receive beams have passed. The receive beams are output to processor 250 for processing. For example, processor 250 may generate images based on the receive beams.

Processor 250 may execute processor-executable program code stored in memory 260 to perform and/or to control other components of system 200 to perform the processes described herein. Processor 250 may comprise a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof, or other currently-known or later-developed device for generating data (e.g., image data) based on beamformed ultrasound samples. In some embodiments, processor 250 includes a dedicated processor for determining tissue displacement.

According to some embodiments, processor 250 is configured to estimate tissue displacement resulting from an ARFI push pulse based on received B-mode signals. The estimation may use correlation, tracking, motion detection, or other techniques. As will be described below, processor 250 may generate an image by mapping normalized displacement values to display values at corresponding image locations. The generated image may be stored in memory 260.

Memory 260 may comprise a non-transitory computer readable storage media such as Random Access Memory and/or non-volatile memory (e.g., Flash memory, hard disk memory). Display 255 may comprise a cathode ray tube display, liquid crystal display, light-emitting diode display, plasma display, or other type of display for displaying images based on image data generated by processor 250. Display 255 may display an image representing the relative elasticity of different locations in a region of interest.

Figure 3:
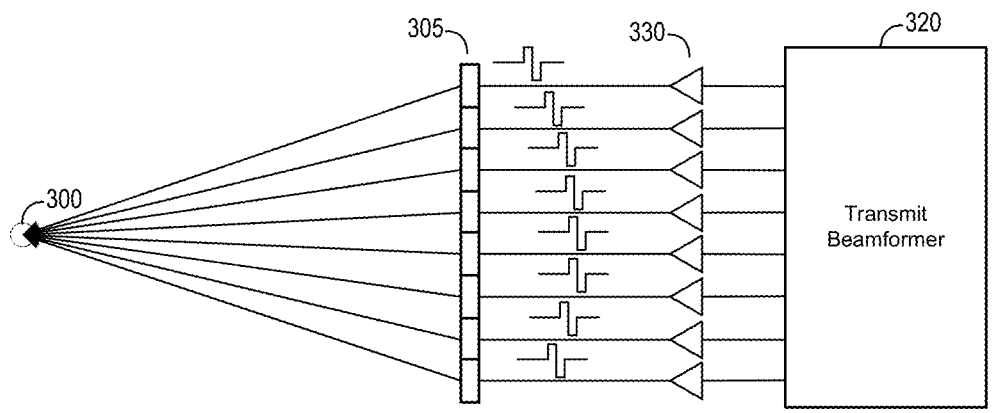
FIG. 3 illustrates transmission of a focused ultrasound pulse according to some embodiments.
Figure 4:
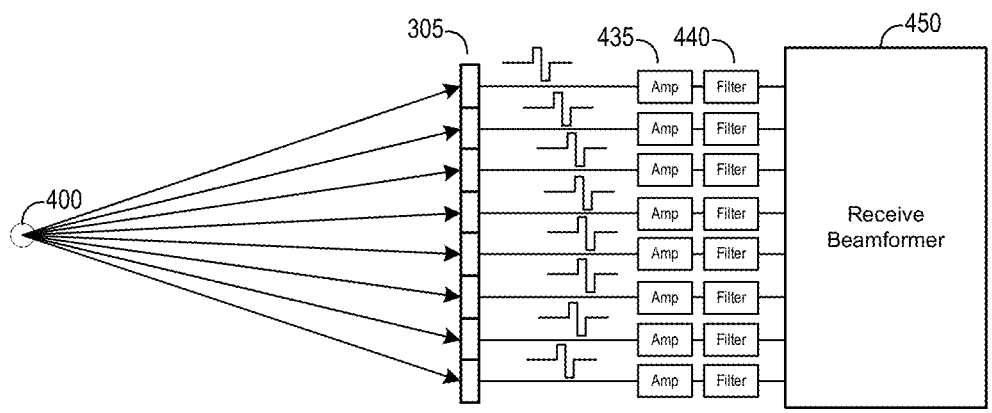
FIG. 4 illustrates focused reception of an ultrasound pulse according to some embodiments.

FIGS. 3 and 4 illustrate focused ultrasound transmission and reception according to some embodiments. Transmit beamformer 320, as shown, controls high-voltage transmitters 330 to produce N (where N=number of transmit channels) respectively-delayed, high-voltage transmit pulses.

These pulses excite individual transducer elements of transducer array 305 to produce an ultrasound beam which is focused at focal area 300.

Transducers of transducer array 305 receive acoustic energy reflected from acoustic impedance discontinuities, and the resulting electrical signals are routed to separate receive channels as shown in FIG. 4. The signals are processed by amplifiers 435 and filters 440 and digitized. Based on a delay profile, the digitized signals are delayed and summed in the receive beamformer 450 in order to generate a receive beamformed signal focused at focal area 400. According to some embodiments, focal areas 300 and 400 are substantially co-located during the transmit/receive sequence described above with respect to beams 160 and 165.

Figure 5:
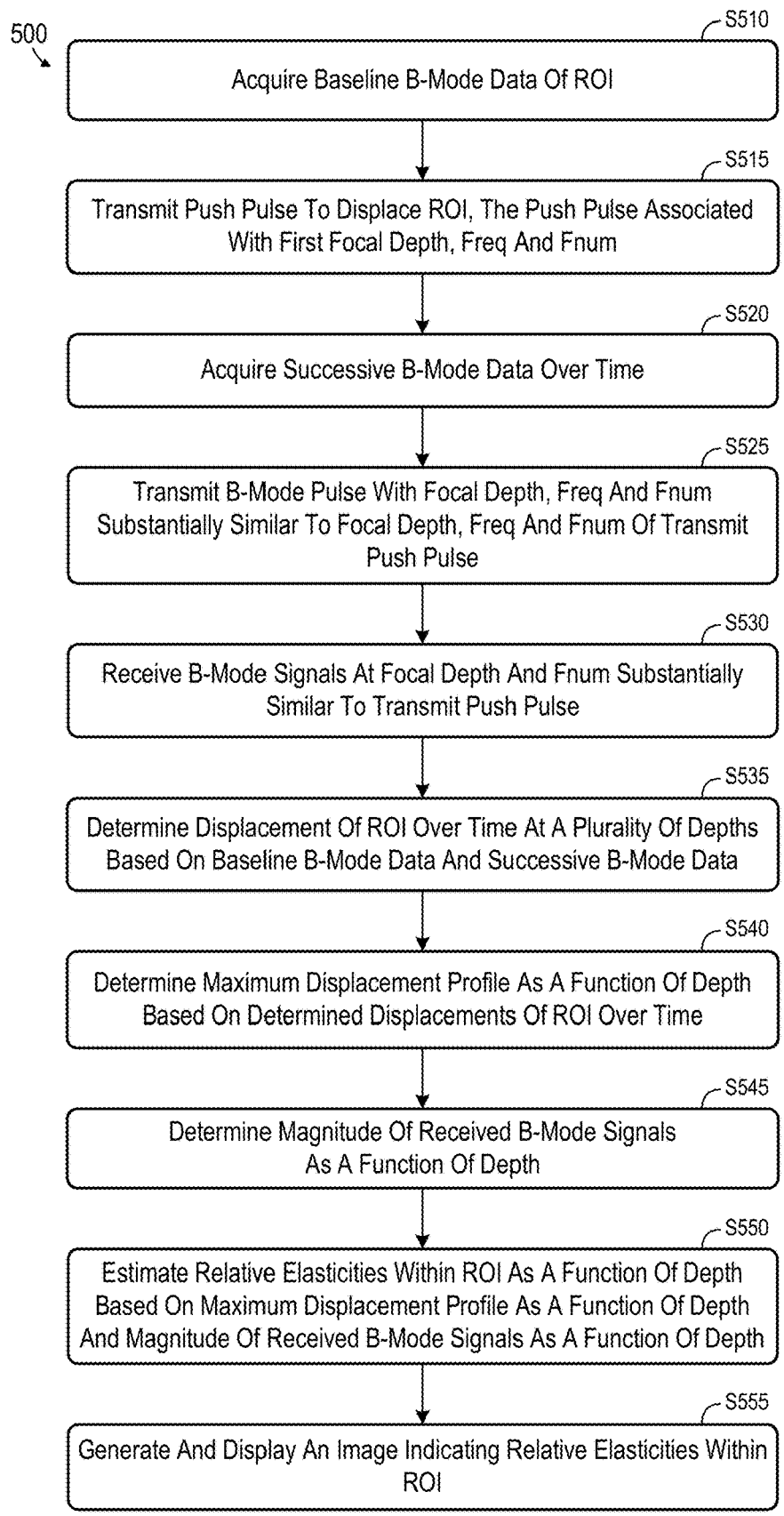
FIG. 5 is a flow diagram of a process to generate a calibrated ARFI image according to some embodiments.

FIG. 5 is a flow diagram of process 500 to generate an image depicting relative elasticity according to some embodiments. Process 500 may be executed by elements of system 200, but embodiments are not limited thereto. Process 500 and all other processes mentioned herein may be embodied in processor-executable program code read from one or more of non-transitory computer-readable media, such as a floppy disk, a CD-ROM, a DVD-ROM, a flash drive, and a magnetic tape, and then stored in a compressed, uncompiled and/or encrypted format. In some embodiments, hard-wired circuitry may be used in place of, or in combination with, program code for implementation of processes according to some embodiments. Embodiments are therefore not limited to any specific combination of hardware and software.

Initially, at S510, baseline B-mode data of an axial line through a region of interest is acquired using one or more pairs of transmit and receive beams as is known in the art. The transit beams may be formed using any beam parameters suitable for acquiring B-mode data. The receive beams may be received using dynamic receive focusing techniques as is known in the art. The baseline B-mode data represents acoustic impedance discontinuities along the axial line.

A push pulse is transmitted at S515 to displace the region of interest. The push pulse is transmitted along the same axis as the beams of S510 and compresses the tissue of the region of interest along the axis. The push pulse is transmitted based on a first frequency, F number/aperture size and, optionally, apodization function. For example, the push pulse may comprise a 400-cycle transmit waveform with a focal depth of 2 cm, Fnum of 2.5 and frequency of 4 MHz, and power amplitude levels similar to or higher than the transmissions used to acquire the B-mode data at S510.

Next, at S520, successive B-mode data is acquired over time. The successive B-mode data is acquired along the same axis and at various intervals during displacement of the tissue. In some embodiments, the successive B-mode data is acquired for 3-5 msec using 1-5 cycle pulses having an Fnum of 1.0 and an intensity of less than 720 mW/cm$^2$ at pulse repetition frequencies between 5 and 10 kHz. As will be described below, tissue displacement caused by the push pulse will be determined based on a comparison of the data acquired at S520 and the data acquired at S510.

A B-mode pulse is transmitted along the axis at S525. The B-mode pulse is transmitted using parameters which are substantially similar to those of the push pulse. In the present example, the B-mode pulse may be transmitted with a focal depth of 2 cm, Fnum of 2.5 and frequency of 4 MHz. The number of cycles of this B-mode pulse may be less than those of the push pulse (e.g., 3.5 cycles).

B-mode signals are received at S530 corresponding to the B-mode pulse transmitted at S525. For example, a receive beamformer forms a receive beam from the received signals based on a focal depth which is fixed at substantially the same focal depth as the B-mode pulse transmitted at S525 (e.g., 2 cm). According to some embodiments, S530 comprises disabling of a dynamic receive focus function of system 200.

Displacement of the region of interest in the axial direction is determined at S535. More specifically, the displacement over time is determined for each of a plurality of depths (i.e., z-positions) based on the baseline B-mode data acquired at S505 and the successive B-mode data acquired at S510. Displacement may be determined by tracking movement of speckle patterns in the pre-push and post-push B-mode data using correlation-based tracking algorithms as known in the art. The resolution of a correlation-based tracking algorithm can be derived from the Cramer-Rao lower bound, and depends upon the signal-to-noise ratio (SNR), the peak correlation and bandwidth of the echoes to be correlated, and the center frequency of the tracking beams. When applied to typical ultrasound data (i.e., SNR=45 dB, p=0.99, BW=70%, $f_0$=7.2 MHz, respectively), the Cramer-Rao lower bound predicts a minimum axial displacement on the order of tenths of a micron.

B-mode data acquired by conventional ultrasound imaging systems may comprise demodulated in-phase and quadrature (IQ) data instead of radio-frequency (RF) data. The IQ data may be remodulated back to RF data and tracked using cross-correlation as discussed above. However, autocorrelation-based methods may be used to compute the displacements directly by estimating the phase shift in the IQ data at each depth over time as is known in the art. The phase shift at each depth represents the localized displacement, restricted to a maximum translation of one-half of the acoustic wavelength to avoid phase wrapping artifacts.

Figure 6:
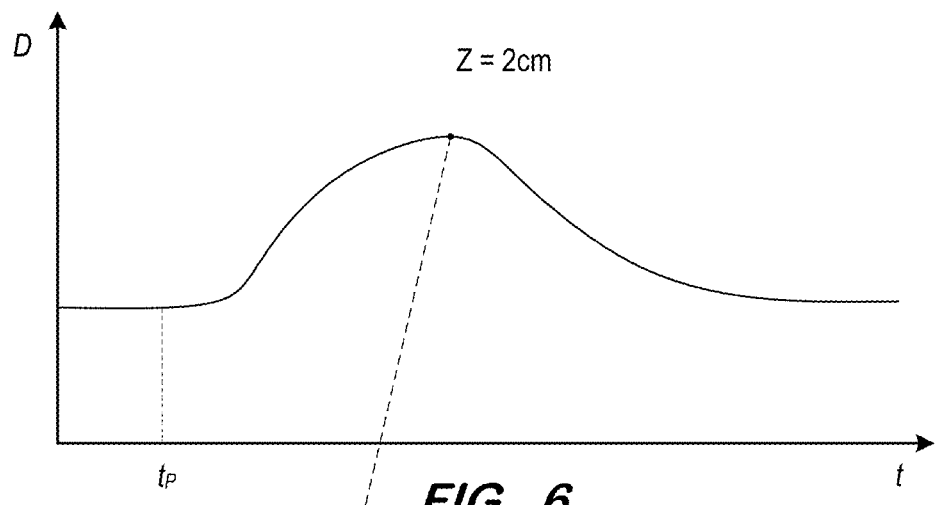
FIG. 6 is a graph of a displacement over time at a fixed on-axis depth according to some embodiments.

FIG. 6 is a graph of a displacement D over time t at a fixed on-axis depth (Z=2 cm) according to some embodiments. The displacement D over time at Z=2 cm may be determined at S535 based on correlation between the data acquired at S510 and S520 as is known in the art. The Time $t_p$ represents the time at which the push pulse was transmitted. Although FIG. 6 illustrates displacement data associated with a single on-axis depth, S535 comprises obtaining displacement data for other on-axis depths.

Figure 7:
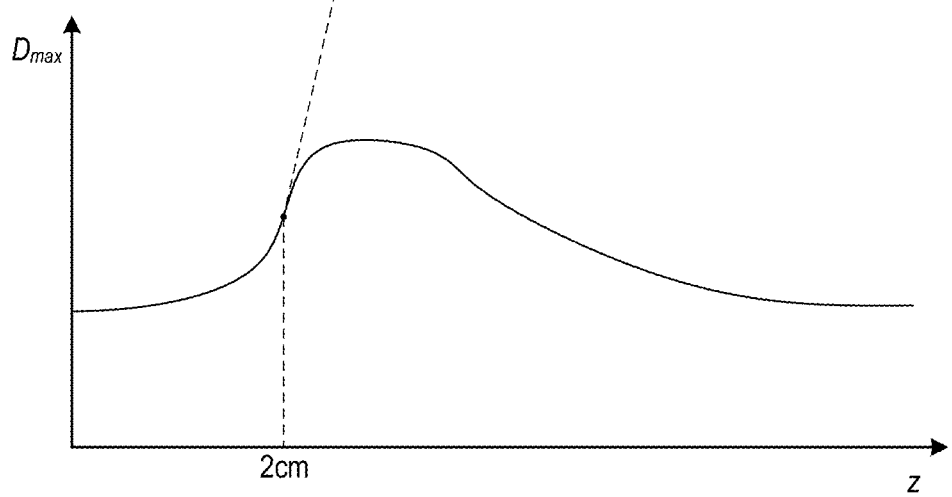
FIG. 7 is a graph of maximum displacement versus on-axis depth according to some embodiments.

The maximum displacement experienced at each depth is determined at S540. The maximum displacement may be determined based on the temporal displacement profiles determined for each of the plurality of depths at S535. FIG. 7 is a profile of maximum displacement versus on-axis depth according to some embodiments. As shown, the FIG. 7 profile plots maximum displacement $D_{max}$ against on-axis depth Z. The maximum value of displacement D in the FIG. 6 graph is plotted on the FIG. 7 profile at Z=2 as shown. The FIG. 7 profile consists of maximum displacement values of each profile determined at S535, plotted at their corresponding Z values.

Next, at S545, the magnitude of the B-mode signals received at S530 is determined as a function of depth as is known in the art (e.g., using envelope detection). According to some embodiments, the magnitude is determined by calculating abs(Hilbert$_z$(RF(x, z))), but embodiments are not limited thereto. In some embodiments, S545 includes compensation for front-end analog gain by dividing the determined magnitude by a depth-dependent gain function (e.g., FeGain(z)).

Figure 8:
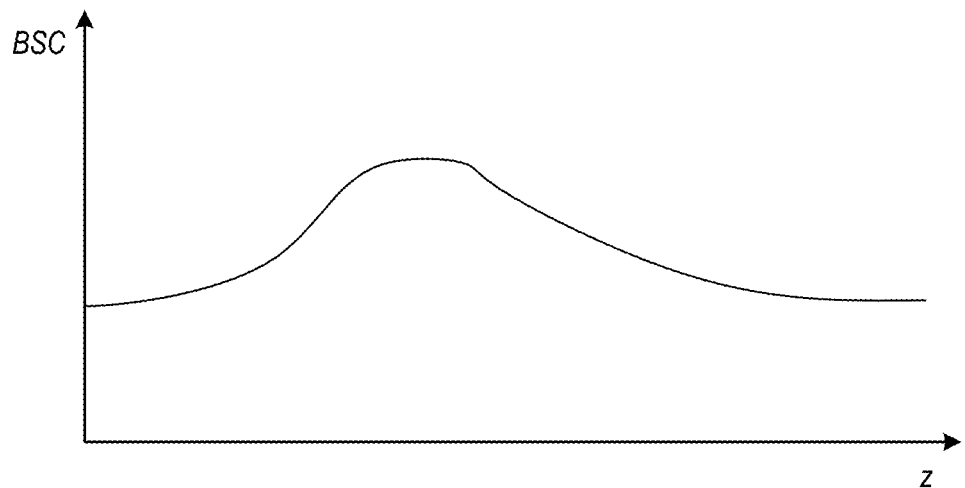
FIG. 8 is a graph of a fixed-focus B-mode receive pulse amplitude versus on-axis depth according to some embodiments.

FIG. 8 is a graph of a fixed-focus B-mode receive pulse amplitude versus on-axis depth according to some embodiments. At S550, relative elasticities within the region of interest are estimated based on the magnitude over depth determined at S545 and the maximum displacement over depth determined at S540.

Figure 9:
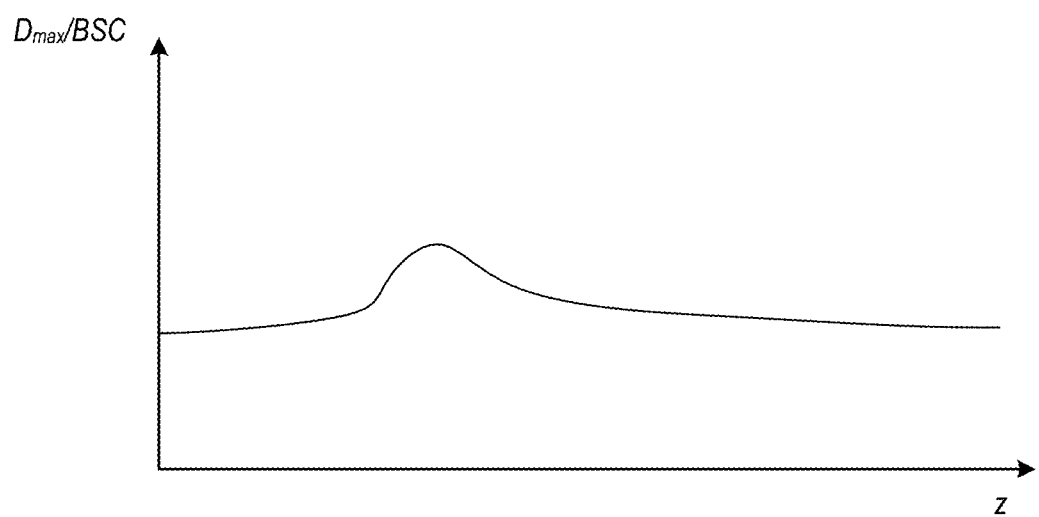
FIG. 9 is a graph of normalized maximum displacement versus on-axis depth according to some embodiments.

According to some embodiments, S550 consists of dividing the maximum displacement profile by the magnitude over depth determined at S545. FIG. 9 is a graph of a thusly-normalized maximum displacement over depth according to some embodiments. As will be described below, the normalized maximum displacement at each depth is inversely proportional to the elasticity of the tissue at that depth. Advantageously, the normalization accounts for the attenuation and diffraction patterns of the actual tissue being imaged.

Particularly, the displacement profile acquired at S535 may be written as displ(z) and is proportional to $E(z)D^2(z) e^{-2\alpha fz}$ as follows: $displ(z) \propto E(z)I_0(z)e^{-2\alpha fz} = E(z)D^2(z)e^{-2\alpha fz}$ where $E(z)$ is a constant related to the elastic properties of the tissue at depth z and inversely proportional to stiffness (E is small=stiff, E is large=soft), $I_0(z)$ is the on-axis intensity profile in absence of attenuation, $D(z)$ is the on-axis transmit beam profile in absence of attenuation (i.e., $I_0(z)=D^2(z)$), f is the beam frequency and $\alpha$ is the attenuation coefficient of the tissue. Accordingly, the exponent $-2\alpha fz$ represents the decrease in intensity due to attenuation along the beam path.

The magnitude determined at S545 may be expressed as $BSC(z)$ and is proportional to $D_{Tx}(z)D_{Rx}(z)e^{-2\alpha fz}$. Because of the identical focus of the transmit and receive beams of S525 and S530, $D_{Tx}(z)=D_{Rx}(z)$. Accordingly, $D_{Tx}(z)D_{Rx}(z) e^{-2\alpha fz} = D^2(z)e^{-2\alpha fz}$, and $BSC(z) \propto D^2(z)e^{-2\alpha fz}$.

Therefore, at S550, we have $displ(z) \propto E(z)D^2(z)e^{-2\alpha fz}$ (from S535) and $BSC(z) \propto D^2(z)e^{-2\alpha fz}$ (from S545). Dividing displ(z) by BSC(z) at S550 cancels out the $D^2(z)e^{-2\alpha fz}$ term, resulting in a normalized displacement as a function of depth which is proportional to $E(z)$, which represents the elastic properties of the tissue in the absence of diffraction and attenuation effects.

Accordingly, the more similar the focal depth, frequency and Fnum of the push pulse to the focal depth, frequency and Fnum of the B-mode pulse, the more effective is the above technique for cancelling out the $D^2(z)e^{-2\alpha fz}$ term, i.e., for minimizing the diffraction and attenuation effects affecting displ(z). Some embodiments therefore employ a B-Mode pulse having a focal depth, frequency and Fnum which are substantially similar to the respective parameters of the push pulse to a degree which provides suitable reduction of the diffraction and attenuation effects. In some embodiments, substantially similar parameter values of the B-Mode pulse may vary by 5 mm, 100 hz, and 0.1 from the respective focal depth, frequency and Fnum of the push pulse. Embodiments are not limited to these ranges.

The normalized displacement is used to generate an image of the axial line at S555. For example, the normalized displacements for each point z on the axial line are mapped to a color, grayscale, brightness, hue, or other characteristic of a display pixel. In some embodiments, a range of colors is mapped such that a first color (e.g., red) indicates greater displacement and a second color (e.g., blue) indicates lesser displacement.

Figure 10:
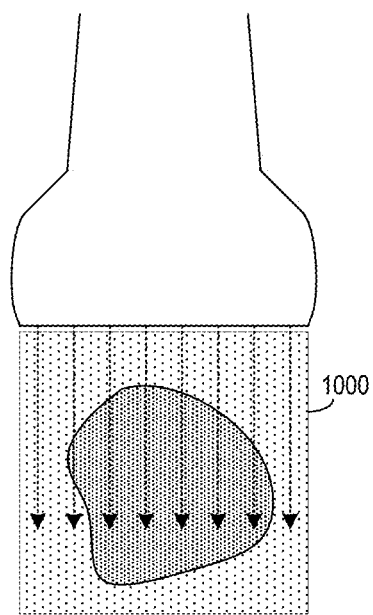
FIG. 10 illustrates acquisition of a two-dimensional ARFI image according to some embodiments.

Process 500 may be repeated for other axial lines through a region of interest, and image data generated for each axial line may be combined into a two-dimensional image. FIG. 10 illustrates push pulses transmitted into volume 1000 and a resulting image generated by executing process 500 with respect to each axial scan line through volume 1000.

Figures 11A, 11B:
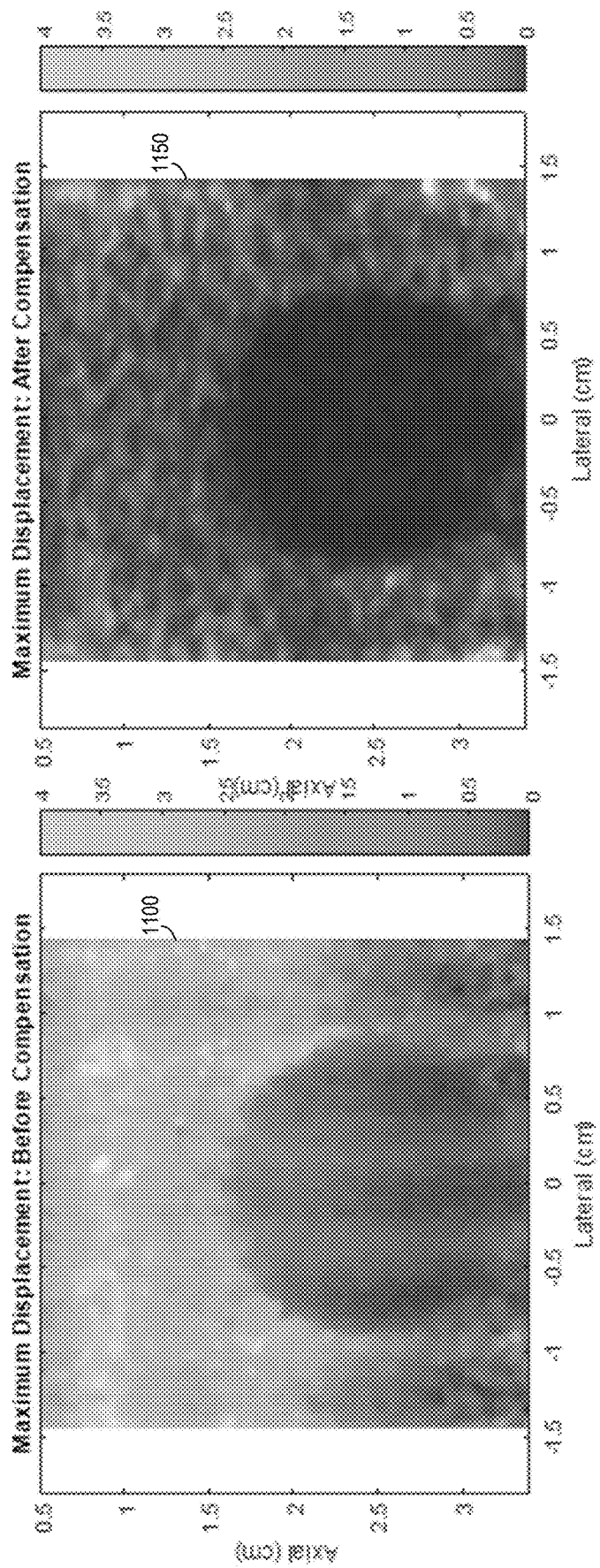
FIG. 11A is a raw image representing maximum displacement.
FIG. 11B is a normalized image representing maximum displacement according to some embodiments.

FIG. 11A depicts displacement image 1100 prior to normalization as described herein. Displacement image 1100 depicts the maximum displacement as a function of depth (as determined at S540) for each of many axial lines. Normalized displacement image 1150 of FIG. 11B depicts, for each axial line, the maximum displacement as a function of depth after normalization based on the magnitude of received B-mode signals as described above. As shown, image 1150 depicts the differences in relative elasticities within the imaged tissue significantly more clearly than image 1100.

According to some embodiments, an elasticity image generated as described herein may be combined and displayed with other image information. For example, the elasticity image may be displayed as a color overlay of a B-mode image. Moreover, known processing techniques may be applied to the image to remove noise, adjust brightness, collimate the field of view, and/or conform the frames to the display properties of a display device.

According to some embodiments, a user may select two or more regions of interest (ROIs) within a displayed elasticity image. For example, one selected ROI may include a lesion and another selected ROI may include normal tissue. A ratio between the elasticity of the regions is then determined and displayed. This ratio may be used to identify lesion type, or to quantify the degree of a condition. By providing more accurate elasticity images, this ratio may be determined more accurately than in prior systems.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A system comprising:
   an ultrasound imaging system configured to:
   transmit an ultrasound push pulse toward material along a first axis, the ultrasound push pulse associated with a first frequency, a first F number, and a first focal depth;
   determine displacement of the material along the first axis in response to the ultrasound push pulse;
   transmit an ultrasound pulse toward the material along the first axis, the second ultrasound pulse associated with a second frequency substantially similar to the first frequency, a second F number substantially similar to the first F number, and a second focal depth substantially similar to the first focal depth;
   receive echo signals from the material in response to the ultrasound pulse;
   form a receive beam from the echo signals using a fixed focal depth substantially equal to the first focal depth;
   determine a magnitude of the receive beam along the first axis;
   determine relative elasticity of the material along the first axis by determining a ratio of the determined displacement of the material by the ultrasound push pulse along the first axis to the magnitude of the receive beam along the first axis; and
   generate an image based on the determined relative elasticity of the material along the first axis.

2. A system according to claim 1, wherein determination of the displacement of the material along the first axis in response to the ultrasound push pulse comprises:
   determination of a maximum displacement at each point of the material along the first axis in response to the push pulse, and
   wherein the relative elasticity of the material along the first axis is determined by dividing the determined maximum displacement of the material along the first axis by the magnitude of the receive beam along the first axis.

3. An ultrasound imaging system comprising:
an ultrasound transducer configured to:
  transmit an ultrasound push pulse toward material along a first axis, the ultrasound push pulse associated with a first frequency, a first F number, and a first focal depth;
  transmit an ultrasound pulse toward the material along the first axis, the ultrasound pulse associated with a second frequency substantially similar to the first frequency, a second F number substantially similar to the first F number, and a second focal depth substantially similar to the first focal depth; and
  receive echo signals from the material in response to the ultrasound pulse;
a receive beamformer configured to:
  form a receive beam from the echo signals using a fixed focal depth substantially similar to the first focal depth; and
a processor configured to:
  determine displacement of the material along the first axis in response to the ultrasound push pulse;
  determine a magnitude of the receive beam along the first axis;
  determine relative elasticity of the material along the first axis by determining a ratio of the determined displacement of the material by the ultrasound push pulse along the first axis to the magnitude of the receive beam along the first axis; and
  determine pixel values of an image at each of a plurality of locations along the first axis based on the determined relative elasticity of the material along the first axis; and
a display configured to display the image.

4. A system according to claim 3, wherein determination of displacement of the material along the first axis in response to the ultrasound push pulse comprises:
  determination of a maximum displacement at each point of the material along the first axis in response to the ultrasound push pulse, and
  wherein the relative elasticity of the material along the first axis is determined by dividing the determined maximum displacement at each point of the material along the first axis by the magnitude of the receive beam along the first axis.

5. A system according to claim 3, the processor further configured to:
  receive a selection of a first region of the image and a second region of the image;
  determine a second ratio between a first relative elasticity of the first region and a second relative elasticity of the second region; and
  display the second ratio on the display.

6. A system according to claim 3, the ultrasound transducer further configured to:
  transmit two or more B-mode ultrasound tracking pulses toward the material along the first axis before transmitting the ultrasound push pulse;
  receive baseline tracking echo signals from the material in response to the two or more B-mode ultrasound tracking pulses;
  transmit two or more B-mode ultrasound pulses toward the material along the first axis after transmitting the ultrasound push pulse and before transmitting the ultrasound pulse; and
  receive displacement tracking echo signals from the material in response to the two or more B-mode ultrasound pulses,
wherein the processor is configured to:
  determine displacement of the material at points along the first axis based on the received baseline tracking echo signals and the received displacement tracking echo signals.

7. A system according to claim 3, the ultrasound transducer further configured to:
  transmit a second ultrasound push pulse toward the material along a second axis, the second ultrasound push pulse associated with a third frequency, a third F number, and a third focal depth;
  transmit a second ultrasound pulse toward the material along the second axis, the second ultrasound pulse associated with a fourth frequency, a fourth F number, and a fourth focal depth substantially similar to the third frequency, the third F number, and the third focal depth, respectively; and
  receive second echo signals from the material in response to the second ultrasound pulse;
the receive beamformer further configured to:
  form a second receive beam from the second echo signals using a second fixed focal depth substantially similar to the third focal depth; and
the processor further configured to:
  determine displacement of the material along the second axis in response to the second ultrasound push pulse;
  determine a magnitude of the second receive beam along the second axis;
  determine relative elasticity of the material along the second axis by determining a ratio of the determined displacement of the material along the second axis to the magnitude of the second receive beam along the second axis; and
  determine pixel values of the image at each of a plurality of locations along the second axis based on the determined relative elasticity of the material along the second axis.

8. A system according to claim 7, wherein the third frequency, third F number, and third focal depth are substantially similar to the first frequency, the first F number, and the first focal depth, respectively.

9. A method comprising:
  transmitting an ultrasound push pulse toward material along a first axis, the ultrasound push pulse associated with a first frequency, a first F number, and a first focal depth;
  determining displacement of the material along the first axis in response to the ultrasound push pulse;
  transmitting an ultrasound pulse toward the material along the first axis, the ultrasound pulse associated with a second frequency substantially similar to the first frequency, a second F number substantially similar to the first F number, and a second focal depth substantially similar to the first focal depth;
  receiving echo signals from the material in response to the ultrasound pulse;
  forming a receive beam from the echo signals using a fixed focal depth substantially similar to the first focal depth;
  determining a magnitude of the receive beam along the first axis;
  determining relative elasticity of the material along the first axis by determining a ratio of the determined displacement of the material by the ultrasound push pulse along the first axis to the magnitude of the receive beam along the first axis; and generating an image based on the determined relative elasticity of the material along the first axis.

10. A method according to claim 9, further comprising:

transmitting two or more B-mode ultrasound tracking pulses toward the material along the first axis before transmitting the ultrasound push pulse;

receiving baseline tracking echo signals from the material in response to the two or more B-mode ultrasound tracking pulses;

transmitting two or more B-mode ultrasound pulses toward the material along the first axis after transmitting the ultrasound push pulse and before transmitting the ultrasound pulse; and receiving displacement tracking echo signals from the material in response to the two or more B-mode ultrasound pulses; and determining displacement at points of the material along the first axis based on the received baseline tracking echo signals and the received displacement tracking echo signals.

11. A method according to claim 9, wherein determining the displacement of the material along the first axis in response to the ultrasound push pulse comprises:

determining a maximum displacement at each point of the material along the first axis in response to the push pulse, and wherein the relative elasticity of the material along the first axis is determined by dividing the determined maximum displacement at each point of the material along the first axis by the magnitude of the receive beam along the first axis.

12. A method to claim 11, further comprising:

receiving a selection of a first region of the image and a second region of the image;

determining a second ratio between a first relative elasticity of the first region and a second relative elasticity of the second region; and displaying the second ratio on the display.

13. A method according to claim 9, further comprising:

transmitting a second ultrasound push pulse toward the material along a second axis, the second ultrasound push pulse associated with a third frequency, a third F number, and a third focal depth;

determining displacement of the material along the second axis in response to the second push pulse;

transmitting a second ultrasound pulse toward the material along the second axis, the second ultrasound pulse associated with a fourth frequency, a fourth F number, and a fourth focal depth substantially similar to the third frequency, the third F number, and the third focal depth, respectively;

receiving second echo signals from the material in response to the second ultrasound pulse;

forming a second receive beam from the second echo signals using a second focal depth substantially equal to the third focal depth;

determining a magnitude of the second receive beam along the second axis; and determining relative elasticity of the material along the second axis by determining a ratio of the determined displacement of the material along the second axis to the magnitude of the second receive beam along the second axis, wherein the image is generated based on the determined relative elasticity of the material along the second axis.

14. A method according to claim 13, wherein the third frequency, third F number, and third focal depth are substantially similar to the first frequency, the first F number, and the first focal depth, respectively.

* * * * *